(12) United States Patent
Stevenson et al.

(10) Patent No.: US 7,732,367 B2
(45) Date of Patent: Jun. 8, 2010

(54) CATALYST FOR METHACROLEIN OXIDATION AND METHOD FOR MAKING AND USING SAME

(75) Inventors: Scott A. Stevenson, Houston, TX (US); Wugeng Liang, Katy, TX (US); James W. Kauffman, Katy, TX (US); Lixia Cai, Maple Glen, PA (US); Angie McGuffey, Sugarland, TX (US); Joseph R. Linzer, Houston, TX (US)

(73) Assignee: Saudi Basic Industries Corporation (SA)

( * ) Notice: Subject to any disclaimer, the term of this patent is extended or adjusted under 35 U.S.C. 154(b) by 1123 days.

(21) Appl. No.: 11/189,095

(22) Filed: Jul. 25, 2005

(65) Prior Publication Data

US 2007/0021629 A1   Jan. 25, 2007

(51) Int. Cl.
| | |
|---|---|
| *B01J 27/00* | (2006.01) |
| *B01J 27/198* | (2006.01) |
| *B01J 27/188* | (2006.01) |
| *B01J 27/19* | (2006.01) |
| *B01J 27/192* | (2006.01) |
| *B01J 27/185* | (2006.01) |
| *B01J 27/182* | (2006.01) |
| *B01J 23/00* | (2006.01) |
| *B01J 23/10* | (2006.01) |
| *B01J 23/32* | (2006.01) |
| *B01J 23/02* | (2006.01) |
| *B01J 23/06* | (2006.01) |
| *B01J 23/04* | (2006.01) |
| *C07C 67/00* | (2006.01) |
| *C07C 51/16* | (2006.01) |
| *C07C 51/235* | (2006.01) |
| *C07C 43/30* | (2006.01) |
| *C07C 43/32* | (2006.01) |

(52) U.S. Cl. .......... 502/208; 502/209; 502/210; 502/211; 502/212; 502/213; 502/214; 502/300; 502/302; 502/305; 502/324; 502/325; 502/340; 502/344; 502/349; 502/353; 562/535; 568/598; 560/208

(58) Field of Classification Search ......... 502/208–214; 562/535
See application file for complete search history.

(56) References Cited

U.S. PATENT DOCUMENTS

| | | | | |
|---|---|---|---|---|
| 3,825,600 | A * | 7/1974 | Ohara et al. .......... | 568/479 |
| 3,907,712 | A | 9/1975 | Ohara et al. .......... | 502/243 |
| 3,928,462 | A | 12/1975 | Shiraishi et al. ...... | 568/480 |
| 3,929,899 | A | 12/1975 | Grasselli et al. ...... | 568/476 |

(Continued)

FOREIGN PATENT DOCUMENTS

EP      0 025 715  B1     3/1981

(Continued)

*Primary Examiner*—Patricia L Hailey
(74) *Attorney, Agent, or Firm*—Robert W. Strozier

(57) ABSTRACT

A catalyst for oxidation of unsaturated and/or saturated aldehyde to unsaturated acids is disclosed where the catalyst including at least molybdenum (Mo), phosphorus (P), vanadium (V), bismuth (Bi), and a first component selected from the group consisting of potassium (K), rubidium (Rb), cesium (Cs), thallium (Tl), or mixtures or combinations thereof, where the catalyst has at least 57% medium pores and a nitric acid to molybdenum mole ratio of at least 0.5:1 or at least 6.0:1 moles of $HNO_3$ per mole of $Mo_{12}$. Methods for making and using such catalysts are also disclosed.

20 Claims, 3 Drawing Sheets

U.S. PATENT DOCUMENTS

| | | | |
|---|---|---|---|
| 3,933,751 A | 1/1976 | Callahan et al. | 568/477 |
| 3,936,505 A | 2/1976 | Oda et al. | 502/215 |
| 3,946,081 A | 3/1976 | Wedemeyer et al. | 568/470 |
| 3,954,856 A | 5/1976 | Kobayashi et al. | 562/538 |
| 3,956,181 A | 5/1976 | Grasselli et al. | 502/212 |
| 3,956,378 A | 5/1976 | Grasselli et al. | 562/546 |
| 3,959,384 A | 5/1976 | Takenaka et al. | 568/479 |
| 3,963,645 A | 6/1976 | Gelbein | 502/248 |
| 3,966,823 A | 6/1976 | Takenaka et al. | 568/479 |
| 3,972,920 A | 8/1976 | Ishii et al. | 562/538 |
| 3,980,709 A | 9/1976 | Kubo et al. | 568/479 |
| 3,984,477 A | 10/1976 | Kubo et al. | 568/479 |
| 3,993,673 A | 11/1976 | McMullen | 549/531 |
| 4,001,317 A | 1/1977 | Grasselli et al. | 562/546 |
| 4,012,449 A | 3/1977 | Shikakura et al. | 568/471 |
| 4,025,565 A | 5/1977 | Oda et al. | 568/477 |
| 4,034,008 A | 7/1977 | Kutz et al. | 562/546 |
| 4,035,418 A | 7/1977 | Okada et al. | 562/538 |
| 4,040,978 A | 8/1977 | Li | 502/212 |
| 4,045,478 A | 8/1977 | Umemura et al. | 562/535 |
| 4,049,577 A | 9/1977 | Childress et al. | 502/178 |
| 4,052,450 A | 10/1977 | Krabetz et al. | 562/546 |
| 4,052,462 A | 10/1977 | Sakakibara et al. | 568/477 |
| 4,060,545 A | 11/1977 | Miller et al. | 560/208 |
| 4,065,507 A | 12/1977 | Hardman et al. | 568/477 |
| 4,066,704 A | 1/1978 | Harris et al. | 568/475 |
| 4,078,004 A | 3/1978 | Schlaefer et al. | 568/479 |
| 4,087,382 A | 5/1978 | Khoobiar | 502/249 |
| 4,111,984 A | 9/1978 | Ishii et al. | 562/538 |
| 4,111,985 A | 9/1978 | Okada et al. | 562/546 |
| 4,118,419 A | 10/1978 | Ishii et al. | 562/534 |
| 4,124,634 A | 11/1978 | Gotoh et al. | 562/532 |
| 4,127,603 A | 11/1978 | Bljumberg et al. | 562/533 |
| 4,129,600 A | 12/1978 | Childress et al. | 568/479 |
| 4,134,859 A | 1/1979 | Kurtz et al. | 502/249 |
| 4,148,757 A | 4/1979 | Brazdil et al. | 502/205 |
| 4,151,117 A | 4/1979 | Schlaefer | 502/212 |
| 4,155,938 A | 5/1979 | Yamamoto et al. | 568/479 |
| 4,162,234 A | 7/1979 | Grasselli et al. | 502/205 |
| 4,166,808 A | 9/1979 | Daumas et al. | 502/249 |
| 4,170,570 A | 10/1979 | Zagata et al. | 502/211 |
| 4,171,328 A | 10/1979 | Umemura et al. | 568/479 |
| 4,171,454 A | 10/1979 | Miller et al. | 562/546 |
| 4,174,354 A | 11/1979 | Grasselli et al. | 585/626 |
| 4,174,459 A | 11/1979 | Sakamoto et al. | 562/534 |
| 4,176,234 A | 11/1979 | Grasselli et al. | 562/546 |
| 4,180,678 A | 12/1979 | Wada et al. | 562/534 |
| 4,182,907 A | 1/1980 | Grasselli et al. | 562/546 |
| 4,184,981 A | 1/1980 | Vanderspurt | 502/209 |
| 4,186,152 A | 1/1980 | Yamamoto et al. | 568/477 |
| 4,190,608 A | 2/1980 | Grasselli et al. | 562/546 |
| 4,195,187 A | 3/1980 | Vanderspurt | 562/545 |
| 4,205,181 A | 5/1980 | Murib | 560/241 |
| 4,208,303 A | 6/1980 | Sasaki et al. | 502/38 |
| 4,209,640 A | 6/1980 | Yamamoto et al. | 562/532 |
| 4,212,767 A | 7/1980 | Daniel | 502/211 |
| 4,217,309 A | 8/1980 | Umemura et al. | 568/477 |
| 4,219,670 A | 8/1980 | Okada et al. | 562/546 |
| 4,224,187 A | 9/1980 | Vanderspurt | 502/212 |
| 4,224,193 A | 9/1980 | Vanderspurt | 502/307 |
| 4,225,466 A | 9/1980 | Wada et al. | 502/209 |
| 4,230,639 A | 10/1980 | Khoobiar | 568/471 |
| 4,230,640 A | 10/1980 | Khoobiar | 568/477 |
| 4,240,931 A | 12/1980 | Milberger et al. | 502/306 |
| 4,245,118 A | 1/1981 | Yamamoto et al. | 562/532 |
| 4,248,803 A | 2/1981 | Vanderspurt | 568/477 |
| 4,250,339 A | 2/1981 | Sakamoto et al. | 568/471 |
| 4,252,683 A | 2/1981 | Khoobiar | 502/211 |
| RE30,545 E | 3/1981 | Khoobiar | 502/249 |
| 4,258,217 A | 3/1981 | Aoshima et al. | 568/474 |
| 4,261,858 A | 4/1981 | Khoobiar | 502/211 |
| 4,267,385 A | 5/1981 | Umemura et al. | 568/479 |
| 4,267,386 A | 5/1981 | Vanderspurt | 568/480 |
| 4,271,040 A | 6/1981 | Khoobiar | 502/211 |
| 4,272,408 A | 6/1981 | Daniel | 502/211 |
| 4,272,637 A | 6/1981 | Yamamoto et al. | 568/780 |
| 4,276,196 A | 6/1981 | Dalton et al. | 502/212 |
| 4,280,928 A | 7/1981 | Kirch et al. | 502/205 |
| 4,280,929 A | 7/1981 | Shaw et al. | 502/215 |
| 4,292,203 A | 9/1981 | Milberger et al. | 502/304 |
| 4,297,247 A | 10/1981 | Krabetz et al. | 502/310 |
| 4,298,763 A | 11/1981 | Engelbach et al. | 568/479 |
| 4,303,550 A | 12/1981 | Callahan et al. | 502/24 |
| 4,306,088 A | 12/1981 | Nakamura et al. | 568/471 |
| 4,306,090 A | 12/1981 | Kirch et al. | 568/481 |
| 4,311,611 A | 1/1982 | Sasaki et al. | 502/22 |
| 4,316,856 A | 2/1982 | Guttmann et al. | 558/322 |
| 4,320,227 A | 3/1982 | Matsumoto et al. | 562/534 |
| 4,321,160 A | 3/1982 | Farrington et al. | 502/209 |
| 4,323,703 A | 4/1982 | Grasselli et al. | 562/546 |
| 4,332,971 A | 6/1982 | Dalton et al. | 568/480 |
| 4,337,364 A | 6/1982 | Solomon | 568/475 |
| 4,339,355 A | 7/1982 | Decker et al. | 502/343 |
| 4,341,900 A | 7/1982 | Ishii et al. | 562/532 |
| 4,351,963 A | 9/1982 | Ray et al. | 568/477 |
| 4,354,044 A | 10/1982 | Aoshima et al. | 568/479 |
| 4,356,316 A | 10/1982 | Aoshima et al. | 560/208 |
| RE31,088 E | 11/1982 | Grasselli et al. | 562/535 |
| 4,370,490 A | 1/1983 | Gruber et al. | 560/214 |
| 4,374,759 A | 2/1983 | Khoobiar | 502/249 |
| 4,377,501 A | 3/1983 | Khoobiar | 502/211 |
| 4,380,664 A | 4/1983 | Ishii et al. | 562/546 |
| 4,388,223 A | 6/1983 | Ferlazzo et al. | 502/211 |
| 4,388,225 A | 6/1983 | Solomon | 502/346 |
| 4,397,771 A | 8/1983 | Grasselli et al. | 502/306 |
| 4,404,397 A | 9/1983 | Daniel | 562/546 |
| 4,413,147 A | 11/1983 | Khoobiar | 568/476 |
| 4,414,134 A | 11/1983 | Friedrich et al. | 502/204 |
| 4,415,482 A | 11/1983 | Ebner | 502/205 |
| 4,419,270 A | 12/1983 | Ueshima et al. | 502/209 |
| 4,424,141 A | 1/1984 | Grasselli et al. | 502/205 |
| 4,425,255 A | 1/1984 | Toyoda et al. | 502/38 |
| 4,442,308 A | 4/1984 | Arntz et al. | 568/480 |
| 4,443,555 A | 4/1984 | Callahan et al. | 502/211 |
| 4,443,556 A | 4/1984 | Aoki et al. | 502/212 |
| 4,444,906 A | 4/1984 | Callahan et al. | 502/211 |
| 4,444,907 A | 4/1984 | Ohdan et al. | 502/211 |
| 4,446,328 A | 5/1984 | Aoshima et al. | 568/479 |
| 4,453,006 A | 6/1984 | Shaw et al. | 562/545 |
| 4,454,346 A | 6/1984 | Khoobiar | 562/535 |
| 4,467,113 A | 8/1984 | Matsumoto et al. | 562/535 |
| 4,471,061 A | 9/1984 | Shaw et al. | 502/34 |
| 4,471,062 A | 9/1984 | Farrington et al. | 502/34 |
| 4,479,013 A | 10/1984 | Khoobiar | 568/479 |
| 4,489,170 A | 12/1984 | Krabetz et al. | 502/211 |
| 4,499,301 A | 2/1985 | Murib | 562/546 |
| 4,503,247 A | 3/1985 | Khoobiar | 562/535 |
| 4,511,671 A | 4/1985 | Saito et al. | 502/242 |
| 4,518,523 A | 5/1985 | Blum et al. | 502/212 |
| 4,528,398 A | 7/1985 | Callahan et al. | 562/534 |
| 4,530,916 A | 7/1985 | Matsumoto et al. | 502/209 |
| 4,532,365 A | 7/1985 | Khoobiar | 568/479 |
| 4,535,188 A | 8/1985 | Khoobiar | 568/479 |
| 4,537,874 A | 8/1985 | Sato et al. | 502/311 |
| 4,537,998 A | 8/1985 | Shum et al. | 568/483 |
| 4,547,588 A | 10/1985 | Khoobiar | 562/535 |
| 4,552,860 A | 11/1985 | Murib | 502/242 |
| 4,556,731 A | 12/1985 | Guttmann et al. | 562/546 |
| 4,558,028 A * | 12/1985 | Tsuneki et al. | 502/211 |
| 4,558,029 A | 12/1985 | Paparizos et al. | 502/211 |
| 4,558,154 A | 12/1985 | Shum et al. | 562/537 |
| RE32,082 E | 2/1986 | Khoobiar | 568/476 |
| 4,585,883 A | 4/1986 | Briggs | 556/42 |
| 4,596,784 A | 6/1986 | Kennelly et al. | 502/209 |

| | | | |
|---|---|---|---|
| 4,621,155 A | 11/1986 | Ueshima et al. | 562/534 |
| 4,652,673 A | 3/1987 | Matsumoto et al. | 562/535 |
| 4,677,084 A | 6/1987 | Bergna | 502/8 |
| 4,720,575 A | 1/1988 | Gruber | 560/214 |
| 4,732,884 A | 3/1988 | Sarumaru et al. | 502/205 |
| 4,778,930 A | 10/1988 | Grasselli et al. | 568/477 |
| 4,803,190 A | 2/1989 | Sarumaru et al. | 502/205 |
| 4,816,603 A | 3/1989 | Oh-Kita et al. | 562/538 |
| 4,855,275 A | 8/1989 | Suresh et al. | 502/353 |
| 4,871,700 A | 10/1989 | Uchida et al. | 502/51 |
| 4,916,103 A | 4/1990 | Martan et al. | 502/212 |
| 4,925,823 A | 5/1990 | Krabetz et al. | 502/211 |
| 4,946,819 A | 8/1990 | Sasaki et al. | 502/214 |
| 4,954,650 A | 9/1990 | Abe et al. | 562/534 |
| 4,968,846 A | 11/1990 | Kuragano et al. | 568/479 |
| 4,985,592 A | 1/1991 | Ishii et al. | 562/534 |
| 5,017,542 A | 5/1991 | Martan et al. | 502/209 |
| 5,059,573 A | 10/1991 | Sasaki et al. | 502/205 |
| 5,072,052 A | 12/1991 | Boeck et al. | 568/479 |
| 5,081,314 A | 1/1992 | Kissel et al. | 568/479 |
| 5,082,819 A | 1/1992 | Boeck et al. | 502/212 |
| 5,094,990 A | 3/1992 | Sasaki et al. | 502/214 |
| 5,102,847 A | 4/1992 | Yamamoto et al. | 502/209 |
| 5,132,269 A | 7/1992 | Sasaki et al. | 502/205 |
| 5,138,100 A | 8/1992 | Matsuura | 568/474 |
| 5,139,988 A | 8/1992 | Sasaki et al. | 502/206 |
| 5,144,090 A | 9/1992 | Honda et al. | 568/476 |
| 5,153,162 A | 10/1992 | Kurimoto et al. | 502/209 |
| 5,155,262 A | 10/1992 | Etzkorn et al. | 562/532 |
| 5,166,119 A | 11/1992 | Oh-Kita et al. | 502/209 |
| 5,173,468 A | 12/1992 | Boehning et al. | 502/209 |
| 5,183,936 A | 2/1993 | Etzkorn et al. | 562/532 |
| 5,198,578 A | 3/1993 | Etzkorn et al. | 562/532 |
| 5,198,579 A * | 3/1993 | Honda et al. | 562/535 |
| 5,198,581 A | 3/1993 | Kawajiri et al. | 562/546 |
| 5,206,431 A | 4/1993 | Hashiba et al. | 562/534 |
| 5,208,371 A | 5/1993 | Kuroda et al. | 562/538 |
| 5,218,146 A | 6/1993 | Takata et al. | 562/535 |
| 5,221,653 A | 6/1993 | Jaeger et al. | 502/212 |
| 5,221,767 A * | 6/1993 | Boehning et al. | 562/532 |
| 5,225,389 A | 7/1993 | Caillod et al. | 502/205 |
| 5,245,083 A | 9/1993 | Matsuura | 568/479 |
| 5,250,485 A | 10/1993 | Kuroda et al. | 502/159 |
| 5,264,627 A | 11/1993 | Tazaki et al. | 562/599 |
| 5,276,178 A | 1/1994 | Onodera et al. | 562/537 |
| 5,300,707 A | 4/1994 | Caillod et al. | 568/480 |
| 5,349,092 A | 9/1994 | Watanabe et al. | 568/480 |
| 5,364,825 A | 11/1994 | Neumann et al. | 502/311 |
| 5,380,933 A | 1/1995 | Ushikubo et al. | 562/549 |
| 5,491,258 A | 2/1996 | Watanabe et al. | 562/538 |
| 5,532,199 A | 7/1996 | Watanabe et al. | 502/311 |
| 5,602,280 A | 2/1997 | Nagai et al. | 562/546 |
| 5,618,974 A | 4/1997 | Kurimoto et al. | 562/532 |
| 5,670,702 A | 9/1997 | Jackson et al. | 560/208 |
| 5,681,790 A | 10/1997 | Kim et al. | 502/164 |
| 5,684,188 A | 11/1997 | Hefner et al. | 562/532 |
| 5,700,752 A | 12/1997 | Kurimoto et al. | 502/311 |
| 5,728,894 A | 3/1998 | Nagano et al. | 568/479 |
| 5,739,391 A | 4/1998 | Ruppel et al. | 562/532 |
| 5,817,865 A | 10/1998 | Machhammer et al. | 560/208 |
| 5,821,390 A | 10/1998 | Ruppel et al. | 568/470 |
| 5,856,259 A | 1/1999 | Watanabe et al. | 502/305 |
| 5,877,108 A | 3/1999 | Suresh et al. | 502/20 |
| 5,892,108 A | 4/1999 | Shiotani et al. | 562/532 |
| 5,929,275 A | 7/1999 | Wada et al. | 562/545 |
| 5,948,683 A | 9/1999 | Koermer et al. | 436/37 |
| 5,981,804 A | 11/1999 | Kurimoto et al. | 568/479 |
| 5,990,348 A | 11/1999 | Lyon et al. | 562/549 |
| 6,028,220 A | 2/2000 | Wada et al. | 562/546 |
| 6,043,184 A | 3/2000 | Karmakar et al. | 502/208 |
| 6,060,419 A | 5/2000 | Wijesekera et al. | 502/208 |
| 6,069,271 A | 5/2000 | Tanimoto et al. | 562/545 |
| 6,171,571 B1 | 1/2001 | Bedard et al. | 423/594.7 |
| 6,387,841 B1 * | 5/2002 | Devlin et al. | 502/208 |
| 2004/0034249 A1 * | 2/2004 | Arnold et al. | 562/547 |

FOREIGN PATENT DOCUMENTS

| | | |
|---|---|---|
| EP | 0 169 449 B1 | 1/1986 |
| EP | 0 223 877 B1 | 6/1987 |
| EP | 0 267 556 B1 | 5/1988 |
| EP | 0 279 374 B1 | 8/1988 |
| EP | 418657 A2 * | 3/1991 |
| EP | 0 450 596 B1 | 10/1991 |
| EP | 0 460 932 B1 | 12/1991 |
| EP | 0 501 794 B1 | 9/1992 |
| EP | 0 523 727 B1 | 1/1993 |
| EP | 0 558 028 B1 | 9/1993 |
| EP | 0 563 025 A1 | 9/1993 |
| EP | 0 574 895 A1 | 12/1993 |
| EP | 0 630 879 A1 | 12/1994 |
| EP | 0 685 260 A2 | 12/1995 |
| EP | 0 767 161 A1 | 4/1997 |
| JP | 2003-010690 * | 1/2003 |
| WO | WO 91/08185 | 6/1991 |

* cited by examiner

CATALYST FOR METHACROLEIN OXIDATION AND METHOD FOR MAKING AND USING SAME

BACKGROUND OF THE INVENTION

1. Field of the Invention

The present invention relates to a heteropolyacid catalyst including rholybdenum (Mo) and phosphorus (P) for use in producing unsaturated acids such as acrylic acid, methacrylic acid or the like in the gas-phase catalytic oxidation of unsaturated aldehydes such as acrolein, methacrolein, or the like or saturated aldehydes such as isobutyraldehyde, where the catalyst is prepared using a nitric acid to molybdenum mole ratio of at least 0.5:1 or a nitric acid to $Mo_{12}$ ratio of at least 6.0:1 during catalyst preparation and/or the catalyst has at least 50% medium pores, preferably at least 57% medium pores, and method for making and using same.

More particularly, the present invention relates to a heteropolyacid catalyst including molybdenum (Mo), phosphorus (P), vanadium (V), bismuth (Bi), and optionally, copper (Cu), an optional first component selected from the group consisting of potassium (K), rubidium (Rb), cesium (Cs), thallium (Tl), or mixtures or combinations thereof, and an optional second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof, used in producing unsaturated acids such as acrylic acid, methacrylic acid or the like by the gas-phase catalytic oxidation of unsaturated aldehydes such as acrolein, methacrolein, or the like or saturated aldehydes such as isobutyraldehyde, where the catalyst is prepared using a nitric acid to molybdenum mole ratio of at least 0.5:1 or a nitric acid to $Mo_{12}$ ratio of at least 6.0:1 during catalyst preparation and/or the catalyst has a pore size distribution comprising at least 50% medium pores, preferably at least 57% medium pores, and method for making and using same.

2. Description of the Related Art

Many, if not all, prior art heteropolyacid catalysts for the production of unsaturated acids from unsaturated aldehydes have taught the use of nitric acid or other strong mineral acids in the preparation of the heteropolyacid catalyst, while certain prior art patents have taught a critical nitric acid ($HNO_3$) concentration for the preparation of heteropolyacid catalysts, especially heteropolyacid catalysts including bismuth as one of the catalyst components. U.S. Pat. No. 5,102,846 discloses a catalyst preparation using a critical amount of $HNO_3$ to form a heteropoly acid with improved activity and to dissolve bismuth nitrate when present, while U.S. Pat. No. 5,102,847 discloses a catalyst made by using at least one bismuth compound selected from the group consisting of bismuth nitrate and bismuth oxide as a source of bismuth and using nitric acid of more than 1 mole to not more than 5 moles based on 12 moles of molybdenum atoms for dissolving the bismuth compound(s). U.S. Pat. No. 6,624,326 discloses a process for producing methacrylic acid through vapor phase oxidation or vapor phase oxydehydrogenation of at least one of methacrolein, isobutyl aldehyde and isobutyric acid in the presence of a heteropolyacid catalyst containing a heteropolyacid composed of at least one of molybdophosphoric acid and molybdovanadophosphoric acid or a salt of the heteropolyacid, characterized in that said heteropolyacid catalyst has been prepared by a method comprising preparing an aqueous solution or aqueous dispersion which (1) contains the nitrogen-containing heterocyclic compound, nitrate anions and ammonium ions, (2) the ammonium ion content not exceeding 1.7 moles per mol of the nitrate anion content, and (3) the ammonium ion content not exceeding 10 moles per 12 moles of the molybdenum atom content, by mixing raw materials containing the catalyst-constituting elements with the nitrogen-containing heterocyclic compound in the presence of water, drying and calcining the same.

Although several methods have been disclosed for preparing catalysts with critical amounts of nitric acid for the formation of heteropoly acid catalysts, especially catalysts containing bismuth, there is still a need in the art for improved catalysts for the gas phase oxidation of unsaturated aldehydes such as acrolein and methacrolein or saturated aldehydes such as isobutyraldehyde to unsaturated acids, such as acrylic acid or methacrylic acid.

DEFINITIONS AND ABBREVIATIONS

The term IBA means isobutanal sometimes also referred to as isobutyraldehyde.

The term MAC means methacrolein.

The term MAA means methacrylic acid.

The term T means temperature.

The term P means pressure.

The term HC means hydrocarbon.

The term aldehyde feedstock means a stream including mixtures of isobutanal and methacrolein.

The term GC means gas chromatography.

The term FID means flame ionization detector of a GC.

The term h or hr or hrs means hours.

The term g means grams.

The term mL means milliliter.

The term min or min. means minutes.

The term wt % or wt. % means weight percent.

The term vol % or vol. % means volume percent.

The term DI water means deionized water.

The term pore volume distribution means a desired concentration of small pores, medium pores and large pores.

The term small pores means pores having a diameter D less than about 100 Å, i.e., D<100 Å.

The term medium pores means pores having a diameter D greater than or equal to about 100 Å and less than about 1000 Å, i.e., 100 Å$\leq$D<1000 Å.

The term large pore volume means pores having a diameter D greater than or equal to about 1000 Å, i.e., D$\geq$1000 Å.

SUMMARY OF THE INVENTION

General Catalyst Compositions

The present invention provides a novel, highly active, heteropolyacid catalyst including at least molybdenum (Mo) and phosphorus (P), adapted to gas-phase oxidize unsaturated and/or saturated aldehydes to unsaturated acids, where the catalyst has a pore size distribution comprising at least 50% medium pores.

The present invention provides a novel, highly active, heteropolyacid catalyst including at least molybdenum (Mo) and phosphorus (P), adapted to gas-phase oxidize unsaturated aldehydes and/or saturated aldehydes to unsaturated acids, where catalyst is prepared using an effective amount of an ammonium-containing compound, where the effective amount is sufficient to increase an amount of medium pores in the resulting catalysts and preferably to produce a pore size distribution comprising at least 57% medium pores in the catalyst.

The present invention provides a novel, highly active, heteropolyacid catalyst including at least molybdenum (Mo) and phosphorus (P), adapted to gas-phase oxidize unsaturated aldehydes and/or saturated aldehydes to unsaturated acids, where the catalyst is prepared using a nitric acid to $Mo_{12}$ mole ratio of at least 6.0:1.

The present invention provides a novel, highly active, heteropolyacid catalyst including at least molybdenum (Mo), phosphorus (P) and an ammonium-containing compound, adapted to gas-phase oxidize unsaturated aldehydes and/or saturated aldehydes to unsaturated acids. The ammonium-containing compound generally increases a number of medium sized pores in the resulting catalyst. When the ammonium-containing compound is basic, then the ammonium-containing compound can be used to adjust a pH of pre-catalyst solutions or slurries allowing the use of greater amount of mineral acid in the catalyst preparation.

The present invention provides a novel, highly active, heteropolyacid catalyst including at least molybdenum (Mo) and phosphorus (P), adapted to gas-phase oxidize unsaturated aldehydes and/or saturated aldehydes to unsaturated acids, where the catalyst is prepared using a nitric acid to $Mo_{12}$ mole ratio of at least 6.0:1 and an effective amount of an ammonium-containing compound, where the amount of nitric acid and the effective amount are sufficient to increase an amount of medium pores in the resulting catalysts and preferably to produce a pore size distribution comprising at least 57% medium pores in the catalyst.

The present invention provides a novel, highly active, heteropolyacid catalyst including at least molybdenum (Mo) and phosphorus (P), adapted to gas-phase oxidize unsaturated aldehydes and/or saturated aldehydes to unsaturated acids, where the catalyst is produced using an amount of nitric acid and an effective amount of ammonium hydroxide and where the amount of nitric acid is sufficient to produce a nitric acid to $Mo_{12}$ mole ratio of at least 6.0:1, where the effective amount of ammonium hydroxide is sufficient to adjust a pH to a desired value of a forming solution or slurry and where the amount of nitric acid and the effective amount of ammonium hydroxide are sufficient to increase an amount of medium pores in the resulting catalysts and preferably to produce a pore size distribution comprising at least 50% medium pores in the catalyst. As used therein, the term "desired pH" means a pH that yields a catalyst composition of this invention that has a pore size distribution having at least 50% medium pores, where the exact pH will depend on the catalyst components as is well known to one of ordinary skill in the art of catalyst preparation.

The present invention provides a novel, highly active, heteropolyacid catalyst including at least molybdenum (Mo), phosphorus (P) and vanadium (V), adapted to gas-phase oxidize unsaturated aldehydes and/or saturated aldehydes to unsaturated acids, where the catalyst has a pore size distribution comprising at least 57% medium pores and is prepared from a pre-catalyst formulation having a nitric acid to $Mo_{12}$ mole ratio of at least 6.0:1 moles and an effective amount of ammonium-containing compound sufficient to adjust the pH to a desired level and/or sufficient to produce the desired pore size distribution.

The present invention provides a novel, highly active, heteropolyacid catalyst including at least molybdenum (Mo), phosphorus (P), vanadium (V) and bismuth (Bi), adapted to gas-phase oxidize unsaturated aldehydes and/or saturated aldehydes to unsaturated acids, where the catalyst has a pore size distribution having an increased amount of medium pores and preferably comprising at least 57% medium pores. The catalyst is prepared from a pre-catalyst formulation having a nitric acid to $Mo_{12}$ mole ratio of at least 6.0:1 moles and an effective amount of an ammonium-containing compound where the amount of the ammonium-containing compound and the amount of nitric acid are sufficient to produce the desired pore size distribution. The effective amount of the ammonium-containing compound, depending on the compound selected, is also sufficient to adjust a pH of the pre-catalyst formulation to a desired pH value.

The present invention provides a novel, highly active, heteropolyacid catalyst including at least molybdenum (Mo), phosphorus (P), vanadium (V), bismuth (Bi), and a first component selected from the group consisting of potassium (K), rubidium (Rb), cesium (Cs), thallium (Tl), or mixtures or combinations thereof, adapted to gas-phase oxidize unsaturated aldehydes and/or saturated aldehydes to unsaturated acids, where the catalyst has a pore size distribution comprising an increased amount of medium pores and preferably at least 57% medium pores. The catalyst is prepared from a pre-catalyst formulation having a nitric acid to $Mo_{12}$ mole ratio of at least 6.0:1 moles and an effective amount of an ammonium-containing compound where the amount of ammonium-containing compound and the amount of nitric acid are sufficient to produce the desired pore size distribution. The effective amount of the ammonium-containing compound, depending on the compound selected, is also sufficient to adjust a pH of the pre-catalyst formulation to a desired pH value.

The present invention also provides a heteropolyacid catalyst including molybdenum (Mo), phosphorus (P), vanadium (V), bismuth (Bi), optionally, copper (Cu), a first component selected from the group consisting of potassium (K), rubidium (Rb), cesium (Cs), thallium (Tl), or mixtures or combinations thereof, and optionally a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof, used for gas-phase catalytic oxidation of unsaturated aldehydes such as acrolein, methacrolein, or the like or saturated aldehydes such as isobutyraldehyde to unsaturated acids such as acrylic acid, methacrylic acid or the like, where the catalyst preferably has a pore size distribution comprising at least 57% medium pores. The catalyst is prepared from a pre-catalyst formulation having a nitric acid to $Mo_{12}$ mole ratio of at least 6.0:1 moles and an effective amount of an ammonium-containing compound where the amount of ammonium-containing compound and the amount of nitric acid are sufficient to produce the desired pore size distribution. The effective amount of the ammonium-containing compound, depending on the compound selected, is also sufficient to adjust a pH of the pre-catalyst formulation to a desired pH value.

In the above catalyst, the unsaturated aldehydes are selected from the group consisting of acrolein, methacrolein, similar unsaturated aldehydes and mixtures or combinations thereof and where the unsaturated acids are selected from the group consisting of acrylic acid, methacrylic acid, similar unsaturated acids, and mixtures or combinations thereof. The saturated aldehydes include isobutyraldehyde or other saturated aldehydes that are convertible to unsaturated acids.

Specific Catalyst Composition I

The present invention also provides a novel, highly active, heteropolyacid catalyst for converting aldehydes to unsaturated acids of the general formula:

$$Mo_{12}P_aV_bCu_cBi_dMI_eMII_fO_g \qquad (I)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.0 and about 5.0,
- c is a number having a value between about 0.0 and about 1.5,
- d is a number having a value between about 0.0 and about 2.0,
- e is a number having a value between about 0.0 and about 2.5,
- f is a number having a value between about 0.0 and about 5.0,
- g is a number having a value representing a sufficient number of oxygen atoms to balance the oxidation state of the catalyst of formula (I),
- if present, the bismuth component is dissolved in a nitric acid solution, where the amount of nitric acid is sufficient to produce a nitric acid to $Mo_{12}$ mole ratio of at least 6.0:1 in a pre-catalyst formulation or during catalyst preparation.

The present invention also provides a novel, highly active, heteropolyacid catalyst for converting aldehydes to unsaturated acids of the general formula:

$$Mo_{12}P_aV_bCu_cBi_dMI_eMII_fO_g \qquad (I)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.0 and about 5.0,
- c is a number having a value between about 0.0 and about 1.5,
- d is a number having a value between about 0.0 and about 2.0,
- e is a number having a value between about 0.0 and about 2.5,
- f is a number having a value between about 0.0 and about 5.0,
- g is a number having a value representing a sufficient number of oxygen atoms to balance the oxidation state of the catalyst of formula (I), and
- the catalyst has a pore size distribution comprising at least 50% medium pores.

The present invention also provides a novel, highly active, heteropolyacid catalyst for converting aldehydes to unsaturated acids of the general formula:

$$Mo_{12}P_aV_bCu_cBi_dMI_eMII_fO_g \qquad (I)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.0 and about 5.0,
- c is a number having a value between about 0.0 and about 1.5,
- d is a number having a value between about 0.0 and about 2.0,
- e is a number having a value between about 0.0 and about 2.5,
- f is a number having a value between about 0.0 and about 5.0, and
- g is a number having a value representing a sufficient number of oxygen atoms to balance the oxidation state of the catalyst of formula (I),
- an effective amount of an ammonium-containing compound is added during catalyst preparation to produce a pore size distribution comprising at least 57% medium pores in the catalyst.

Specific Catalyst Composition II

The present invention also provides a novel, highly active, heteropolyacid catalyst for converting aldehydes to unsaturated acids of the general formula:

$$Mo_{12}P_aV_bCu_cBi_dMI_eMII_fO_g \qquad (II)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5, b is a number having a value between about 0.01 and about 5.0, c is a number having a value between about 0.01 and about 1.5, d is a number having a value between about 0.01 and about 2.0, e is a number having a value between about 0.01 and about 2.5, f is a number having a value between about 0.01 and about 5.0, g is a number having a value representing a sufficient number of oxygen atoms to balance the oxidation state of the catalyst of formula (II), the bismuth component is dissolved in a nitric acid solution having an amount of nitric acid sufficient to produce a nitric acid to $Mo_{12}$ mole ratio of at least 6.0:1, and an effective amount of an ammonium-containing compound is added during catalyst preparation sufficient to produce a pore size distribution comprising at least 50% medium pores in the catalyst.

Specific Catalyst Composition III

The present invention also provides a novel, highly active, heteropolyacid catalyst for converting aldehydes to unsaturated acids of the general formula:

$$Mo_{12}P_aV_bCu_cBi_dMI_eMII_fO_g \quad (III)$$

where:
MI is selected from the group consisting of potassium (K), rubidium (Rb), cesium (Cs), thallium (Tl), and mixtures or combinations thereof, MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof, a is a number having a value between about 0.5 and about 3.5, b is a number having a value between about 0.1 and about 5.0, c is a number having a value between about 0.05 and about 1.5, d is a number having a value between about 0.1 and about 2.0, e is a number having a value between about 0.1 and about 2.5, f is a number having a value between about 0.1 and about 5.0, g is a number having a value representing a sufficient number of oxygen atoms to balance the oxidation state of the catalyst of formula (III), and the bismuth component is dissolved in a nitric acid solution having an amount of nitric acid sufficient to produce a nitric acid to $Mo_{12}$ mole ratio of at least 6.0:1, and an effective amount of an ammonium-containing compound is added during catalyst preparation sufficient to produce a pore size distribution comprising at least 57% medium pores in the catalyst.

Specific Catalyst Composition IV

The present invention also provides a novel, highly active, heteropolyacid catalyst for converting aldehydes to unsaturated acids of the general formula:

$$Mo_{12}P_aV_bCu_cBi_dMI_eMII_fO_g \quad (IV)$$

where:
MI is selected from the group consisting of potassium (K), rubidium (Rb), cesium (Cs), thallium (Tl), and mixtures or combinations thereof, at least two elements MII selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof, a is a number having a value between about 1.0 and about 2.5, b is a number having a value between about 0.1 and about 2.5, c is a number having a value between about 0.05 and about 0.5, d is a number having a value between about 0.1 and about 1.0, e is a number having a value between about 0.2 and about 2.0, f is a number having a value between about 0.3 and about 2.0, g is a number having a value representing a sufficient number of oxygen atoms to balance the oxidation state of the catalyst of formula (IV), and the bismuth component is dissolved in a nitric acid solution having an amount of nitric acid sufficient to produce a nitric acid to $Mo_{12}$ mole ratio of at least 6.0:1, and an effective amount of an ammonium-containing compound is added during catalyst preparation sufficient to produce a pore size distribution comprising at least 50% medium pores, preferably at least 57% medium pores, in the catalyst.

Methods for Preparing Catalysts

The present invention provides a method for preparing a novel, highly active, heteropolyacid catalyst for converting aldehydes to unsaturated acids. The references to moles used in describing the preparation of the catalysts of this invention mean relative molar amounts, e.g., if 1 mole of catalyst is being prepared, the catalyst will have moles of components such that the molar ratio of molybdenum in the catalyst is 12 relative to all other components. As another example, to make a catalyst having the formula $Mo_{12}P_aV_bCu_cBi_dMI_eMII_fO_g$, the number of moles of components used during catalyst preparation will be in a molar ratio of 12:a:b:c:d:e:f:g.

The method includes the step of forming a pre-catalyst composition including 12 moles of molybdenum (1 mole of $Mo_{12}$), a moles of phosphorus (P) and an effective amount of an ammonium-containing compound, where a is a number having a value between about 0.5 and about 3.5, where the pre-catalyst composition can be a solution, a slurry, a suspension, a dispersion or other solid-liquid mixture, corresponding to a catalyst of Formula (I) with b-f equal to zero. The pre-catalyst composition is then evaporated to form a dried catalytic material, which is then calcined to form a catalyst of this invention, where the effective amount of the ammonium-containing compound is sufficient to produce a pore size distribution comprising at least 50% medium pores, preferably 57% medium pores, in the catalyst.

The present invention provides a method for preparing a novel, highly active, heteropolyacid catalyst for converting aldehydes to unsaturated acids including the steps of forming a pre-catalyst composition including 12 moles of molybdenum (1 mole of $Mo_{12}$), a moles of phosphorus (P), b moles of vanadium (V), and an effective amount of an ammonium-containing compound, where a is a number having a value between about 0.5 and about 3.5 and b is a number having a value between about 0.01 and about 5.0, corresponding to a catalyst of Formula (I) with c-f equal to zero. The pre-catalyst composition is then evaporated to form a dried catalytic material, which is then calcined to form a catalyst of this invention, where the effective amount of the ammonium-containing compound is sufficient to produce a pore size distribution comprising at least 50% medium pores, preferably 57% medium pores, in the catalyst.

The present invention provides a method for preparing a novel, highly active, heteropolyacid catalyst for converting aldehydes to unsaturated acids including the steps of forming a substantially solids free solution including 12 moles of molybdenum (1 mole of $Mo_{12}$), a moles of phosphorus (P) and b moles of vanadium (V), where a is a number having a value between about 0.5 and about 3.5 and b is a number having a value between about 0.01 and about 5.0. Prior to, simultaneous with or after the formation of the first solution, dissolving d moles of a bismuth (Bi) compound with an amount of nitric acid and an effective amount of an ammonium-containing compound, preferably ammonium hydroxide, where d is a number having a value between about 0.1 and about 1.0 and when the ammonium-containing compound is ammonium hydroxide, the effective amount of the ammonium-containing compound is sufficient to adjust the pH to a desired pH value. The bismuth solution is then added to the first solution resulting in component precipitation to form a slurry, where the amount of nitric acid is sufficient so that the slurry has a nitric acid to $Mo_{12}$ ratio of at least 6.0 to 1.0 (i.e., ≧6.0 moles of nitric acid per mole of $Mo_{12}$, or ≧1 mole of nitric acid per 2 moles molybdenum or ≧0.5 moles of nitric acid per mole of molybdenum). The slurry is then evaporated to form a dried catalytic material, which is then calcined to form a catalyst of this invention and where the effective amount of the ammonium-containing compound is also sufficient to produce a pore size distribution comprising at least 50% medium pores, preferably 57% medium pores, in the catalyst. This catalyst composition corresponds to a catalyst of Formula (I) with c, e, and f equal to zero.

The present invention provides a method for preparing a novel, highly active, heteropolyacid catalyst for converting aldehydes to unsaturated acids including the steps of forming a first, substantially solid free solution including 12 moles of molybdenum (1 mole of $Mo_{12}$), a moles of phosphorus (P), b moles of vanadium (V), and e moles of a first component selected from the group consisting of potassium (K), rubidium (Rb), cesium (Cs), thallium (Tl), or mixtures or combinations thereof, where a is a number having a value between about 0.5 and about 3.5, b is a number having a value between about 0.01 and about 5.0, and e is a number having a value between about 0.2 and about 2.5. Prior to, simultaneous with or after the formation of the first solution, dissolving d moles of a bismuth (Bi) compound with an amount of nitric acid and an effective amount of an ammoniun-containing compound, preferably, ammonium hydroxide, where d is a number having a value between about 0.1 and about 1.0, when the ammonium-containing compound is ammonium hydroxide, the effective amount of the ammonium-containing compound is sufficient to adjust the pH to a desired pH value. The bismuth solution is then added to the first solution resulting in component precipitation to form a slurry, where the amount of nitric acid is sufficient so that the slurry has a nitric acid to $Mo_{12}$ ratio of at least 6.0 to 1.0 (i.e., ≧6.0 moles of nitric acid per mole of $Mo_{12}$, or ≧1 mole of nitric acid per 2 moles of molybdenum or ≧0.5 moles of nitric acid per mole of molybdenum). Preferably, if the first component is cesium, then the cesium is added to the first solution. The slurry is then evaporated to form a dried catalytic material, which is then calcined to form a catalyst of this invention and where the effective amount of the ammonium-containing compound is also sufficient to produce a pore size distribution comprising at least 50% medium pores, preferably 57% medium pores, in the catalyst. This catalyst composition corresponds to a catalyst of Formula (I) with c and f equal to zero.

The present invention provides a method for preparing a novel, highly active, heteropolyacid catalyst for converting aldehydes to unsaturated acids including the step of forming a first, substantially solids free solution including 12 moles of molybdenum (1 mole of $Mo_{12}$), a moles of phosphorus (P), b moles of vanadium (V), c moles of copper (Cu), e moles of a first component selected from the group consisting of potassium (K), rubidium (Rb), cesium (Cs), thallium (Tl), or mixtures or combinations thereof and f moles of a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof provided that each such second component substantially dissolves in the first solution, where a is a number having a value between about 0.5 and about 3.5, b is a number having a value between about 0.01 and about 5.0, e is a number having a value between about 0.01 and about 2.5, and f is a number having a value between about 0.01 and about 5.0. Prior to, simultaneous with or after the formation of the first solution, d moles of a bismuth (Bi) compound are dissolved in a nitric solution having a sufficient amount of nitric acid to dissolve the bismuth compound, where d is a number having a value between about 0.01 and about 2.0. Prior to, simultaneous with or after the addition of the bismuth compound to the nitric acid solution, an effective amount of an ammonium-containing compound, preferably ammonium hydroxide, is added. When the ammonium-containing compound is ammonium hydroxide, the effective amount of the ammonium-containing compound is sufficient to adjust the pH to a desired pH value. The bismuth solution is then added to the first solution resulting in component precipitation to form a pre-catalyst composition, where the amount of nitric acid is sufficient so that the slurry has a nitric acid to $Mo_{12}$ ratio of at least 6.0 to 1.0 (i.e., ≧6.0 moles of nitric acid per mole of $Mo_{12}$, or ≧1 mole of nitric acid per 2 moles of molybdenum or ≧0.5 moles of nitric acid per mole of molybdenum). The resulting pre-catalyst composition is then heated to about 95° C. and f moles of other second components or mixtures or combinations thereof, are added to the pre-catalyst composition. Although the other first and/or second components or mixtures or combinations thereof as described here are added to the heated pre-catalyst composition, they could equally well have been added to the bismuth solution or to the solid after precipitation of the other components. In many cases, depending on the specific compounds used, catalytic components can be added to the first solution, the bismuth solution or to the slurry with or without heating or even to the catalytic material before calcining. Preferably, if the first component is cesium, then the cesium is added to the first solution. The resulting composition is then evaporated to form a dried catalytic material, which is then calcined to form a catalyst of this invention, and where the effective amount of the ammonium-containing compound is also sufficient to increase an amount of medium pores in the resulting catalysts and preferably to produce a pore size distribution comprising at least 50% medium pores, preferably 57% medium pores, in the catalyst. This catalyst composition corresponds to a catalyst of Formula (II). In an analogous manner, catalyst of Formulas (III) and (IV) can be prepared with the moles of each component being added within their designated ranges.

Methods for Producing Unsaturated Acids

The present invention also provides a method for preparing unsaturated acids including the step of contacting an unsaturated aldehyde with a catalyst of this invention to form a corresponding unsaturated acid, where the method is ideally suited for the production of acrylic acid from acrolein or methacrylic acid from methacrolein, isobutyraldehyde, or similar aldehydes or both.

The present invention provides a method for preparing unsaturated acids including the step of contacting an appropriate alkene with a mixed metal oxide catalyst to form a corresponding unsaturated aldehyde and subsequently contacting the unsaturated aldehyde with a catalyst of this invention to form a corresponding unsaturated acid, where the method is ideally suited for the production of acrylic acid and/or methacrylic acid.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
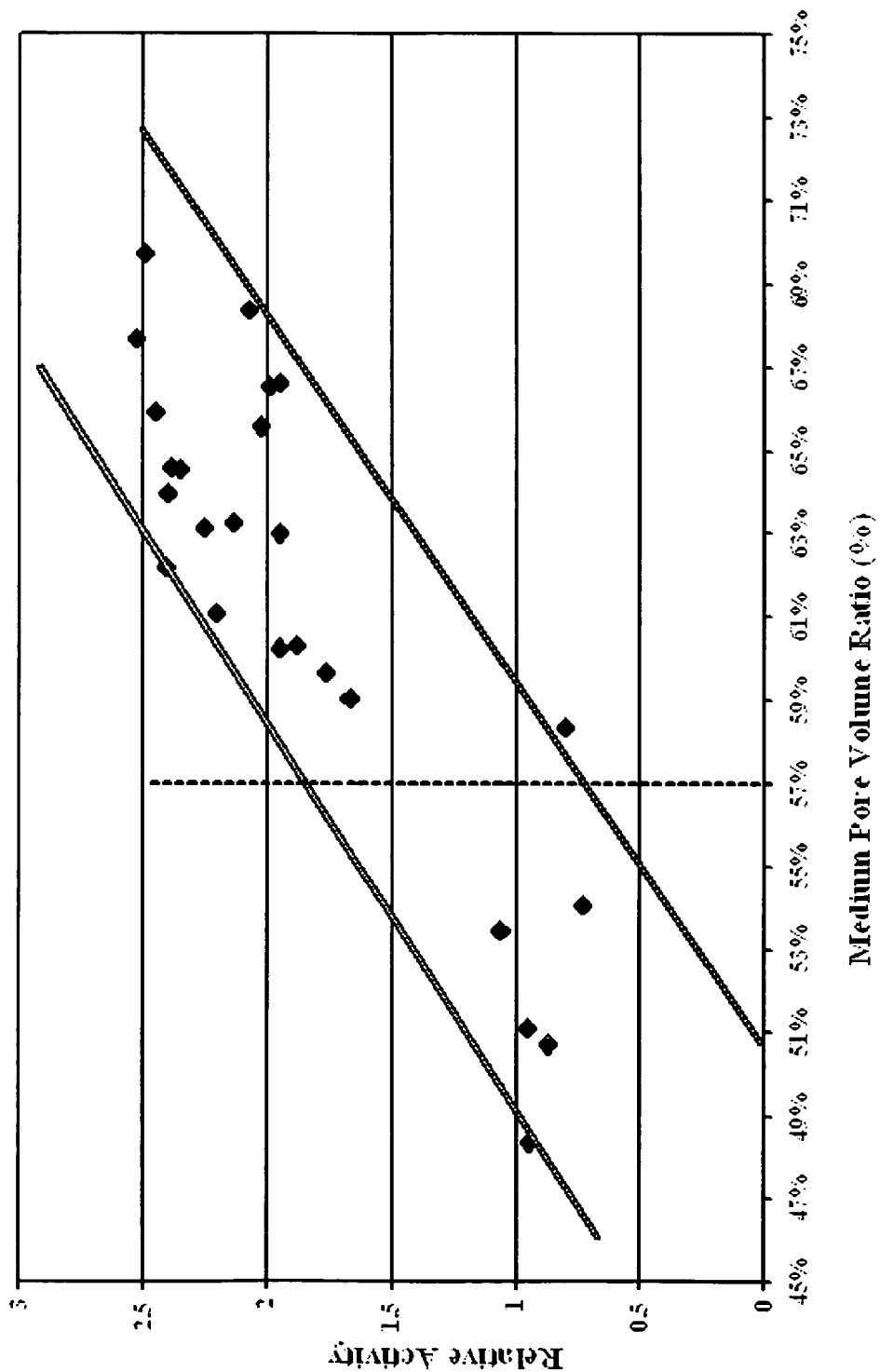
FIG. 1 depicts a graph of the relative activity versus % medium pores.

The inventors have found that a novel, highly active, heteropolyacid catalyst of the general formula:

  (I)

where:

MI is selected from the group consisting of potassium (K), rubidium (Rb), cesium (Cs), thallium (Tl), or mixtures or combinations thereof, MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof, a is a number having a value between about 0.5 and about 3.5, b is a number having a value between about 0.0 and about 5.0, c is a number having a value between about 0.0 and about 1.5, d is a number having a value between about 0.0 and about 2.0, e is a number having a value between about 0.0 and about 2.5, f is a number having a value between about 0.0 and about 5.0, g is a number having a value representing a sufficient number of oxygen atoms to balance the oxidation state of the catalyst of formula (I), if present, the bismuth component is dissolved in a solution having sufficient nitric acid so that the catalyst precursor solution or slurry has a nitric acid to $Mo_{12}$ mole ratio of at least 6.0:1, an effective amount of an ammonium-containing compound, preferably ammonium hydroxide, the effective amount sufficient to produce a catalyst having a pore size distribution comprising of at least 57% medium pores and, when the ammonium-containing compound is ammonium hydroxide, to also adjust a pH of the catalyst precursor solution or slurry to a desired pH value, and the catalysts are uniquely designed for the oxidation of aldehydes into unsaturated acids, especially, for the oxidation of conjugated unsaturated aldehydes or isobutyraldehyde into unsaturated acids.

The inventors have found that the catalysts of Formula (I) can be prepared by a method, where the pH is adjusted by a nitric acid/ammonium hydroxide solution having sufficient nitric acid to provide a nitric acid to molybdenum ratio of $\geqq 1.0$ mole of nitric acid per 2 moles of molybdenum or a nitric acid to $Mo_{12}$ ratio of $\geqq 6.0:1$. If a bismuth component is included in the catalyst preparation, then the bismuth component is dissolved in the nitric acid or a nitric acid/ammonium hydroxide solution, prior to adding the solution to a solution of the other components. Thus, the ammonium-containing compound can be added to either solution if bismuth is included. However, in the absence of bismuth, the ammonium-containing compound is added to a mixture of some or all of the other components to change the pore size distribution of the resulting catalyst. Generally, a mole ratio of the molybdenum-containing compound to the ammonium-containing compound ($Mo:NH_4$) is between about 0.0 to about 20.0 and between about 0.5 to about 20.0 for catalysts regardless of the molybdenum to nitric acid mole ratio. Preferably, the mole ratio is between about 1.0 to about 15.0, and, particularly, the mole ratio is between about 2.0 to about 10.0. Alternatively, a mole ratio of the ammonium-containing compounds to nitric acid ($NH_4:HNO_3$) is between about 0.0 and about 2.0 and between about 0.1 and about 2.0 for catalysts regardless of the molybdenum to nitric acid mole ratio, preferably, between about 0.2 and about 1.8, particularly, between about 0.4 and about 1.6, and more particularly, between about 0.6 and about 1.4 and especially, between about 0.6 and about 1.2. The catalysts preferably have at least 57% medium pores, which is formed during a controlled calcination process.

The present invention broadly relates a novel, highly active, heteropolyacid catalyst including at least molybdenum (Mo), phosphorus (P), vanadium (V), bismuth (Bi), and a first component selected from the group consisting of potassium (K), rubidium (Rb), cesium (Cs), thallium (Tl), or mixtures or combinations thereof, adapted to gas-phase oxidize aldehydes, especially conjugated unsaturated aldehydes or isobutyraldehyde, to unsaturated acids, where the catalyst optionally has at least 57% medium pores and a nitric acid to molybdenum mole ratio of at least 0.5:1 or at least 6.0:1 moles of $HNO_3$ per mole of $Mo_2$. The catalysts are especially well suited for oxidatively converting aldehydes selected from the group consisting of acrolein, methacrolein, similar unsaturated aldehydes, isobutyraldehyde and mixtures or combinations thereof to unsaturated acids selected from the group consisting of acrylic acid, methacrylic acid, similar unsaturated acids, and mixtures or combinations thereof. Preferably, the present invention relates to a heteropolyacid catalyst including molybdenum (Mo), phosphorus (P), vanadium (V), bismuth (Bi), and optionally, copper (Cu), a first component selected from the group consisting of potassium (K), rubidium (Rb), cesium (Cs), thallium (Tl), or mixtures or combinations thereof, and an optional second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof, used for gas-phase catalytic oxidation of aldehydes such as acrolein, methacrolein, isobutyraldehyde or the like to unsaturated acids such as acrylic acid, methacrylic acid or the like. Particularly, the present invention relates to a novel, highly active, heteropolyacid catalyst for converting aldehydes to unsaturated acids of the general formula:

$$Mo_{12}P_aV_bCu_cBi_dMI_eMII_fO_g \qquad (I)$$

where:
MI is selected from the group consisting of potassium (K), rubidium (Rb), cesium (Cs), thallium (Tl), and mixtures or combinations thereof,
MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
a is a number having a value between about 0.5 and about 3.5,
b is a number having a value between about 0.0 and about 5.0,
c is a number having a value between about 0.0 and about 1.5,
d is a number having a value between about 0.0 and about 2.0,
e is a number having a value between about 0.0 and about 2.5,
f is a number having a value between about 0.0 and about 5.0,
g is a number having a value representing a sufficient number of oxygen atoms to balance the oxidation state of the catalyst of formula (I), and
the catalyst is prepared from a mixture having at least six moles of nitric acid per twelve moles of molybdenum and if present, the bismuth component is dissolved in a nitric acid solution to form a bismuth solution prior to adding it to a solution of some or all of the other components. Preferably, the bismuth solution has sufficient nitric acid to produce the at least six moles of nitric acid per twelve moles of molybdenum when the bismuth solution is added to the solution of all or some of the other components.

Suitable compounds used for preparation of the catalysts of this invention include, without limitation, metal nitrates, metal carbonates, metal ammonium salts, metal halides, metal oxides, or mixtures or combinations thereof. For example, suitable molybdenum components include, without limitation, ammonium paramolybdate, molybdenum trioxide, molybdenum chloride, etc. or mixtures or combinations thereof. The preferred molybdenum component is ammonium paramolybdate. Suitable vanadium components include, without limitation, ammonium metavanadate, vanadium pentoxide, vanadium chloride, etc. or mixtures or combinations thereof. The preferred vanadium component is ammonium metavanadate. Suitable phosphorus components include, without limitation, phosphoric acid, ammonium phosphate, etc. or mixtures or combinations thereof. The preferred phosphorus component is phosphoric acid. Suitable copper components include, without limitation, copper nitrate, copper chloride, etc. or mixtures or combinations thereof. The preferred copper component is copper nitrate. Suitable bismuth components include, without limitation, bismuth nitrate, bismuth oxide, bismuth chloride, etc. or mixtures or combinations thereof. The preferred bismuth component is bismuth nitrate. Suitable MI components include, without limitation, MI nitrates, MI oxides, MI chlorides, etc. or mixtures or combinations thereof. The preferred MI components are MI nitrates and MI oxides or mixtures or combinations thereof. Suitable MII components include, without limitation, MII nitrates, MII oxides, MII chlorides, etc. or mixtures or combinations thereof. The preferred MII components are MII nitrates and MII oxides or mixtures or combinations thereof.

Suitable ammonium-containing compounds for use in this invention include, without limitation, any ammonium compound that undergoes thermal decomposition to volatile components. Exemplary examples of such ammonium-containing compounds include, without limitation, ammonium hydroxide, ammonium nitrate, ammonium chloride, ammonium bromide, ammonium carbonate, ammonium acetate, ammonium formate, ammonium propionate, ammonium butionate, other ammonium salts of carboxylic acids, or mixtures or combinations thereof.

Catalyst Preparation Aspects

With Bi free catalysts, the catalysts of this invention are generally prepared by initiating precipitation of a substantially precipitate free solution by means known in the art, e.g., heating and/or solvent evaporation, where the solution includes appropriate concentrations of desired catalytic components. While the solution preferably is substantially free of precipitates prior to initiating precipitation, the solution can include varying degrees of precipitates during the preparation procedure provided that the precipitates substantially dissolve prior to initiating precipitation. For catalysts of this invention including Bi, a slurry is formed when a substantially solid-free Bi solution is added to a substantially solid-free solution of other ingredients. Other ingredients can be added to the slurry or to the solid after drying followed by further drying, but prior to calcination. The term substantially solid-free means that the amount of precipitate present in the solution is less than 5 wt. %, preferably less than 2.5 wt. %, particularly less than 1 wt. % and especially less than 0.5 wt. %, with the ultimate goal being completely solid-free or precipitate-free.

The present invention relates to improved catalysts for the oxidation of aldehydes, where the catalysts of this invention are prepared from a precursor formulation having a nitric acid to $Mo_{12}$ mole ratio greater than or equal to ($\geq$) 6.0:1. Preferably, the solution also includes sufficient ammonium hydroxide to adjust the pH to a desired level and to increase an amount of medium pores in the resulting catalysts and preferably to produce a catalyst having a pore size distribution comprising at least 57% medium pores.

The catalysts of this invention are prepared using a solution of nitric acid ($HNO_3$) and ammonium hydroxide ($NH_4OH$) to dissolve a bismuth component such as bismuth nitrate ($Bi(NO_3)_3$), bismuth oxide or other bismuth salts, prior to adding the bismuth component to a solution of the other components. The bismuth solution and the solution of some or all of the other components are substantially free of precipitates. If bismuth is not used in the catalyst preparation, then the nitric acid/ammonium hydroxide solution was adjusted to produce the desired nitric acid to molybdenum mole ratio and a desired pH of the pre-catalyst solution. Also if the catalyst does not include Bi, then the mixture is preferably a solid-free solution prior to initiating precipitation. Nitric acid referred to here means nitric acid added in producing the catalyst and excludes $NO_3$ moieties which may be part of the molecular formula for the catalytic components used in preparing the catalysts of this invention. As stated previously, the nitric acid is present in an amount sufficient to produce a nitric acid to $Mo_{12}$ ratio of at least 6.0:1 ($\geq 6.0$ to 1.0), while the ammonium hydroxide is present in an amount sufficient to achieve a desired pH. Both the nitric acid and the ammonium hydroxide concentrations are also individually or collectively sufficient to generate a catalyst having a pore size distribution comprising at least 57% medium pores. Although the catalysts of this invention are preferably prepared using water as the solvent, i.e., the liquid phase is an aqueous liquid phase, the catalysts of this invention can be made using a mixed aqueous/organic liquid phase, a mixed aqueous/non-aqueous liquid phase, non-aqueous liquid phase or organic liquid phase. The term organic means a carbon containing solvent, while the term non-aqueous means a non-aqueous solvent that does not contain carbon. The term substantially solid-free means that the amount of precipitate present in the solution is less than 5 wt. %, preferably less than 2.5 wt. %, particularly less than 1 wt. % and especially less than 0.5 wt. %, with the ultimate goal being completely solid-free or precipitate-free.

Catalysts of this invention generally have a given pore size distribution comprising small pores, medium pores, and large pores. Small pores are pores having a diameter D less than about 100 Å, i.e., D<100 Å. Medium pores are pores having a diameter D greater than or equal to about 100 Å and less than about 1000 Å, i.e., 100 Å$\leq$D<100 Å. Large pores are pores having a diameter D greater than or equal to about 1000 Å, i.e., D$\geq$1000 Å. The catalysts of this invention generally have a pore size distribution comprising between about 0.1% and about 10.0% small pores, between about 55% and about 90% medium pores and the remainder large pores. Preferably, the catalysts of this invention have a pore size distribution comprising between about 0.5% and about 7.5% of small pores, between about 55% and about 80% pores, and the remainder large pores. Particularly, the catalysts of this invention have a pore size distribution comprising between about 1.0% and about 5.0% small pores, at least 57% medium pores and the remainder large pores. Alternatively, the catalysts of this invention have a pore size distribution comprising at least 55% medium pores. Preferably, the catalysts of this invention have a pore size distribution comprising between about 55% medium pores and about 90% medium pores. Particularly, the catalysts of this invention have a pore size distribution comprising between about 55% medium pores and about 80% pores. More particularly, the catalysts of this invention have a pore size distribution comprising between about 57% medium pores and about 80% medium pores. It should be recognized by an ordinary artisan that determining or measuring the pore size or pore size distribution of the catalyst can be based on any standard method such as BET, mercury porosimeter, or similar pore size analyzer.

The catalyst of this invention are rendered more or less active by a calcination procedure to which they are subjected. The general calcination protocol is to calcine a dried catalyst at a temperature and for a time sufficient to obtain a catalyst having a desired activity, generally maximized activity or to obtain a catalyst having the desired pore size distribution. Generally, the calcination temperature is above about 350° C. and the period of time is between about 2 hours and about 24 hours; however, shorter and longer times can be used. Preferably, the calcination protocol also includes a soak step at a soak temperature and for a soak time sufficient to out-gas volatile components and components that form volatile components at high temperature. Particularly important components that produce volatile components during drying, soaking and calcining include nitrates and ammonium salts. The inventors believe that although the amount of nitrate and ammonium ions present in the dried composition is important for producing the desired pore size distribution, the careful control of drying, soaking and calcining conditions is also important in controlling the number of medium pores generated in the final catalyst. If the pre-calcined catalyst is heated too fast, the volatile components have insufficient time to out-gas and the activity of the resulting catalyst is reduced. Thus, by controlling catalyst drying, soaking and calcining, component out-gassing can be substantially completed before the catalyst is subjected to its final calcination temperature. The soak temperature is generally between about 180° C. and about 250° C. and the soak period of time is between about 1 hour and about 8 hours; however, shorter and longer times can be used. The soak step is designed to allow volatile components and components that form volatile components at high temperature to exit the catalyst gradually and not explosively or so rapidly that the catalyst pore distribution is damaged (collapses or produces too many large pores). In laboratory protocols, the protocols include an initial temperature ramp of about 0.25° C./min. to about 0.75° C./min. for a period of time sufficient to raise the temperature to a desired soak step temperature and a final temperature ramp of about 0.25° C./min. to about 0.75° C./min for a period of time sufficient to raise the temperature to a desired calcination step temperature. In commercial catalyst protocols, however, the ramp rates are generally much higher as is well known in the art of commercial catalyst preparation.

The catalyst used in the process of the present invention can be used without a carrier, or can be supported on or diluted with an inert carrier. Suitable inert carriers include, without limitation, silicates, silicas, aluminates, aluminas, silica-aluminas, silicon carbide, zirconias, titanias, magnesia, similar oxides, other heteropolyacids or mixtures or combinations thereof.

The catalysts of this invention are ideally suited for producing an unsaturated acid, preferably a conjugated unsaturated acid such as acrylic acid and/or methacrylic acid by gas-phase catalytic oxidation of a vapor or vapor stream including an unsaturated aldehyde, preferably, a conjugated unsaturated aldehyde such as acrolein and/or methacrolein at a temperature, at a pressure and for a time sufficient to obtain a desired conversion of the unsaturated aldehyde to the corresponding unsaturated acid. The vapor stream used to contact the catalysts of the present invention generally includes sufficient unsaturated conjugated aldehyde that is converted into an output stream containing commercial quantity of a corresponding unsaturated conjugated aldehyde. For methacrolein, the vapor stream can have a wide methacrolein concentration range, preferably, the vapor or vapor stream includes from about 1 vol. % to about 20 vol. % of methacrolein, and particularly, the vapor or vapor stream includes from about 2 to about 8 vol. % of methacrolein. Typically, a methacrolein feed for the preparation of methacrylic acid may also contain large amounts of water and smaller amounts of impurities such as carbon monoxide, carbon dioxide, acetone, acetic acid, acrolein, methacrylic acid, isobutylene and other saturated and unsaturated hydrocarbons, lower saturated aldehydes, etc., but such impurities have substantially no effect on the conversion of the aldehydes to unsaturated acids.

Although the gas-phase catalytic oxidation reaction of acrolein or methacrolein over a catalyst of this invention can be economically performed in the presence of air, preferably, an oxidizing agent enriched in oxygen is used such as pure oxygen. An oxygen concentration in the oxidizing gas used in the conversion of methacrolein to methacrylic acid, for example, is set relative to a molar ratio of oxygen to methacrolein. Generally, the molar ratio has a value between about 0.3 and about 4, preferably, the ratio has a value between about 0.8 and about 2.5. The oxidizing gas may be diluted with or contain an inert gas such as nitrogen, steam, carbon dioxide, etc., recycled oxygen-containing gases or mixtures or combinations thereof.

In producing methacrylic acid using the catalysts of this invention, the oxidation is generally carried out at a reaction pressure between sub-ambient and several atmospheres above ambient, preferably, the pressure is near ambient or as low as practical. The oxidation reaction using the catalysts of this invention is generally carried out at an elevated temperature, preferably, at a temperature between about 230° C. and about 450° C., particularly, at a temperature between about 250° C. and about 400° C. and more particularly, at a temperature between about 250° C. and about 350° C. The oxidation reaction using the catalysts of this invention can be carried out using a variety of reactor systems including a fixed bed reactor (a reactor having one or more fixed catalyst beds or zones), a fluidized bed reactor (recycling catalyst particles in the reactor are fluidized), a moving bed reactor (catalyst moves in and out of the catalyst zone(s)), a continuous stirred tank reactor or any other reactor system geared for carrying out an oxidizing reaction such as the conversion of aldehydes to unsaturated acids.

EXPERIMENTAL SECTION

General Considerations

The following examples illustrate the preparation, calcination and testing of specific catalytic formulations of the general formula (I) and of a comparative example catalyst. Example 1 illustrates the preparation of a catalyst of this invention, while Comparative Example 1 illustrates the preparation of a comparative catalyst. Examples are also included that analyze the calcination and performance data for the catalysts of this invention and the comparative example reported herein as relative data. The activity of the comparative example catalyst was defined as 1.0, so that if a catalyst showed an activity 30% higher than the comparative example catalyst, then this catalyst would have a relative activity of 1.3. Similarly, the relative selectivity of a comparative example was defined as 0.0. The selectivity vs. conversion curve is compared between a catalyst of this invention and the comparative example catalyst, so that if the catalyst of this invention showed a selectivity 1.0% higher than comparative example catalyst at the same percentage conversion of methacrolein, then, this catalyst would have a relative selectivity of 1.0. In the following examples, when the term nitric acid is used that term means about a 70 wt. % aqueous solution of nitric acid. It should be recognized by ordinary artisans that any concentrated nitric acid solution can be used provided that the amount added is adjusted to achieve the desired mole ratio. Also in the following examples, when the term phosphoric acid is used the term means about an 85 wt. % phosphoric acid solution. It should be recognized by ordinary artisans that any concentrated phosphoric acid solution can be used provided that the amount added is adjusted to achieve the desired mole ratio.

Catalysts Preparations

Example 1

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$.

46.49 grams of ammonium paramolybdate were added to 200 mL of de-ionized (DI) water at room temperature. 1.28 grams of ammonium metavanadate were added to the above solution to produce an MoV solution. The mixture was stirred at room temperature until all particles were dissolved. 4.28 grams of cesium nitrate were then added to 25 mL of DI water, and the resulting solution was added to the MoV solution to form an MoVCs solution. 3.80 grams of phosphoric acid were then dissolved in 6 mL of DI water and the solution obtained was added to the MoVCs solution to form an MoVCsP solution. 0.51 grams of copper nitrate were added to 5 mL of DI water and the solution obtained was added to the MoVCsP solution to form an MoVCsPCu solution. 11.32 grams of nitric acid were added to 30 grams of DI water, then 7 mL of ammonium hydroxide (28 wt. % solution of ammonia in water) were added to the nitric acid solution and then 5.32 grams of bismuth nitrate were added to the nitric acid/ammonium hydroxide solution and the mixture was stirred until the bismuth nitrate dissolved or went into solution. The bismuth solution was then added to the MoVCsPCu solution forming a MoVCsPCuBi slurry. The MoVCsPCuBi slurry was then heated to 95° C. and 2.56 grams of antimony trioxide and 0.68 grams of boric acid were added to the MoVCsPCuBi slurry to form an MoVCsPCuBiSbB slurry.

The MoVCsPCuBiSbB slurry was then evaporated at between about 75° C. and about 100° C. to form an evaporated mixture. The evaporated mixture was then dried at about 130° C. for about 16 hours and sieved to obtain particles having a size between about 20 and 30 mesh. The particles were then heated to a soak temperature of 230° C. at a rate of 0.5° C./min. and held at the soak temperature for 3 hours in air. The particles were then heated to a calcination temperature of 380° C. at a rate of 0.5° C./min. for 5 hours in air to form the catalyst of this invention.

Example 2

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but calcined at 380° C. for 7.5 hrs instead of 380° C. for 5.0 hrs.

Example 3

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but calcined at 380° C. for 10 hrs instead of 380° C. for 5.0 hrs.

Example 4

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but 5 mL of ammonium hydroxide was used instead of 7 mL of ammonium hydroxide.

Example 5

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but 8 mL of ammonium hydroxide was used instead of 7 mL of ammonium hydroxide.

Example 6

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but 10 mL of ammonium hydroxide was used instead of 7 mL of ammonium hydroxide.

Example 7

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but 14.8 grams of nitric acid and 10 mL of ammonium hydroxide was used instead of 11.32 grams of nitric acid and 7 mL of ammonium hydroxide.

Example 8

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but the relative concentration of the final solution was 1.5 times more concentrated.

Example 9

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, Cu was increased from 0.51 g to 1.59 g and Bi was reduced from 5.32 g to 1.10 g.

Example 10

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, Sb was increased from 2.56 g to 3.74 g.

Example 11

The following example illustrates the calcination of a catalyst of Example 1 having the following formula $Mo_{12}P_{1.5}V_{0.5}Cu_{0.1}Bi_{0.5}Sb_{0.8}Cs_{1.0}B_{0.5}O_g$, where the dinitrification step is carried out at 220° C. for 3 hrs.

Example 12

The following example illustrates the calcination of a catalyst of Example 1 having the following formula $Mo_{12}P_{1.5}V_{0.5}Cu_{0.1}Bi_{0.5}Sb_{0.8}Cs_{1.0}B_{0.5}O_g$, where the dinitrification step is carried out at 230° C. for 3 hrs.

Comparative Example 1

The following comparative example illustrates the preparation of a comparative catalyst for purposes of comparing the catalyst of Example 1, where the comparative catalyst has a formula $Mo_{12}P_{1.5}V_{0.5}Cu_{0.1}Bi_{0.5}Sb_{0.8}Cs_{1.0}B_{0.5}O_g$ identical to that of the catalyst of Example 1, with the exception that the catalyst preparation does not include at least a 6.0:1 mole ratio of nitric acid to $Mo_{12}$ and does not include ammonium hydroxide.

46.50 grams of ammonium paramolybdate were added to 200 mL of de-ionized (DI) water at room temperature. 1.28 grams of ammonium metavanadate were added to the above solution to produce a MoV solution. The mixture was stirred at room temperature until all particles were dissolved. 4.28 grams of cesium nitrate were then added to 25 mL of DI water, and the resulting solution was added to the MoV solution to form a MoVCs solution. 3.80 grams of phosphoric acid were then dissolved in 6 mL of DI water and the solution obtained was added to the MoVCs solution to form a MoVCsP solution. 0.51 grams of copper nitrate were added to 5 mL of DI water and the solution obtained was added to the MoVCsP solution to form a MoVCsPCu solution. 4.30 grams of nitric acid were added to 30 mL of DI water, then 5.32 grams of bismuth nitrate were added and the mixture was stirred until the bismuth nitrate went into solution forming a bismuth solution. The bismuth solution was then added to the MoVCsPCu solution forming a MoVCsPCuBi slurry. The MoVCsPCuBi slurry was then heated to 95° C. and then 2.56 grams of antimony trioxide and 0.68 grams of boric acid were added to the MoVCsPCuBi slurry to form a MoVCsPCuBiSbB slurry.

The MoVCsPCuBiSbB slurry was then evaporated at between about 75° C. and about 100° C. to form a evaporated mixture. The evaporated mixture was then dried at about 130° C. for about 16 hours and sieved to obtain particles having a size between about 20 and 30 mesh. The particles were then heated to a soak temperature of 230° C. at a rate of 0.5° C./min and held at the soak temperature for 3 hours in air. The particles were then heated to a calcination temperature of 380° C. at a rate of 0.5° C./min. for 5 hours in air to form comparative catalyst 1.

Catalyst Testing and Performance Data 6 cc of either the Example 1 or the Comparative Example 1 catalyst were diluted with 9 cc of quartz chip and were loaded into a fixed bed reactor. The catalysts were tested with a vapor stream having the following composition: 4 vol. % methacrolein, 8 vol. % oxygen, and 30 vol. % steam with the balance being nitrogen. By varying reaction temperature and vapor stream flow rate, conversion and selectivity data were obtained under a variety of conditions. The resulting effluent stream was analyzed by gas chromatography.

To understand the following results, the following definitions are set forth:

% conversion={[(moles of MAC converted)]/[(moles of unconverted MAC+moles of MAC converted]}*100

% selectivity={[(moles of MAA produced)]/[(moles of all products produced)]}*100 where MAA is methacrylic acid, MAC is methacrolein and the moles of all products produced is on a four-carbon product count.

The Comparative Example 1 catalyst was tested under three conditions of flow rate in sccm at three different temperatures. The resulting data is tabulated in Table I.

TABLE I

Catalytic Performance of Comparative Example 1 Catalyst

| Flowrate (sccm) | Temperature (°C.) | Conversion (%) | Selectivity (%) |
|---|---|---|---|
| 100 | 290 | 61.3 | 87.0 |
| 57 | 299 | 88.6 | 83.5 |
| 50 | 298 | 93.9 | 82.1 |

The Example 1-10 catalysts and the Comparative Example 1 catalyst were tested under similar flow rate and reaction temperature conditions. The resulting data is tabulated in Table II.

TABLE II

Catalytic Performance of Examples 1-10 Catalysts

| Catalyst | Relative Activity | Relative Selectivity |
|---|---|---|
| Comparative Example 1 | 1.0 | 0.0 |
| Example 1 | 2.5 | 0.0 |
| Example 2 | 2.5 | 0.0 |
| Example 3 | 2.7 | −0.5 |
| Example 4 | 1.6 | 3.5 |
| Example 5 | 2.5 | 2.5 |
| Example 6 | 3.0 | 1.5 |
| Example 7 | 2.6 | 0.0 |
| Example 8 | 2.5 | 2.0 |
| Example 9 | 2.5 | 3.0 |
| Example 10 | 1.8 | −0.5 |

The error in the relative activity data is about ±10% and the error in relative selectivity is about ±1.

The results of Table II clearly shows that much higher catalyst activity is achieved for catalysts prepared by the procedure of Example 1.

The results of variations in the calcination protocol for catalysts of this invention are set forth in Tables III and IV.

TABLE III

Effect of De-nitrification Temperature on Catalyst Performance of Samples of Example 1 Catalyst

| CatalystSample | De-Ni Process | Relative Activity |
|---|---|---|
| Example 1 | 210° C. for 3 hrs | 2.5 |
| Example 11 | 220° C. for 3 hrs | 2.4 |
| Example 12 | 230° C. for 3 hrs | 2.2 |

TABLE IV

Effect of Calcination Time on Catalyst Performance of Samples of Example 1-3 Catalysts

| Catalyst | Calcination Process | Relative Activity |
|---|---|---|
| Example 1 | 380° C. for 5 hrs | 2.5 |
| Example 2 | 380° C. for 7.5 hrs | 2.5 |
| Example 3 | 380° C. for 10 hrs | 2.7 |

Referring now to FIG. 1, a plot of relative activity versus % medium pores is shown for catalyst samples of this invention prepared to vary the percentage of medium pores in the catalysts. The plot clearly shows that the catalysts having a percentage of medium pores of greater than about 57% generally represent superior catalysts to catalysts having a percentage of medium pores of less than about 57%. The data clearly shows that superior catalysts can be prepared having a percentage of medium pores between about 57% and about 71%, preferably, and between about 59% and about 71%, but catalysts with higher percentages of medium pores can also be prepared using the catalyst preparation methodology set forth in this application—the combination of nitric acid at a mole ratio of at least 6.0:1 to one mole of $Mo_{12}$ and a sufficient amount of an ammonium-containing compound to increase an amount of medium pores in the resulting catalysts and preferably to produce catalysts with a pore size distribution having at least 57% medium pores.

Figure 2:
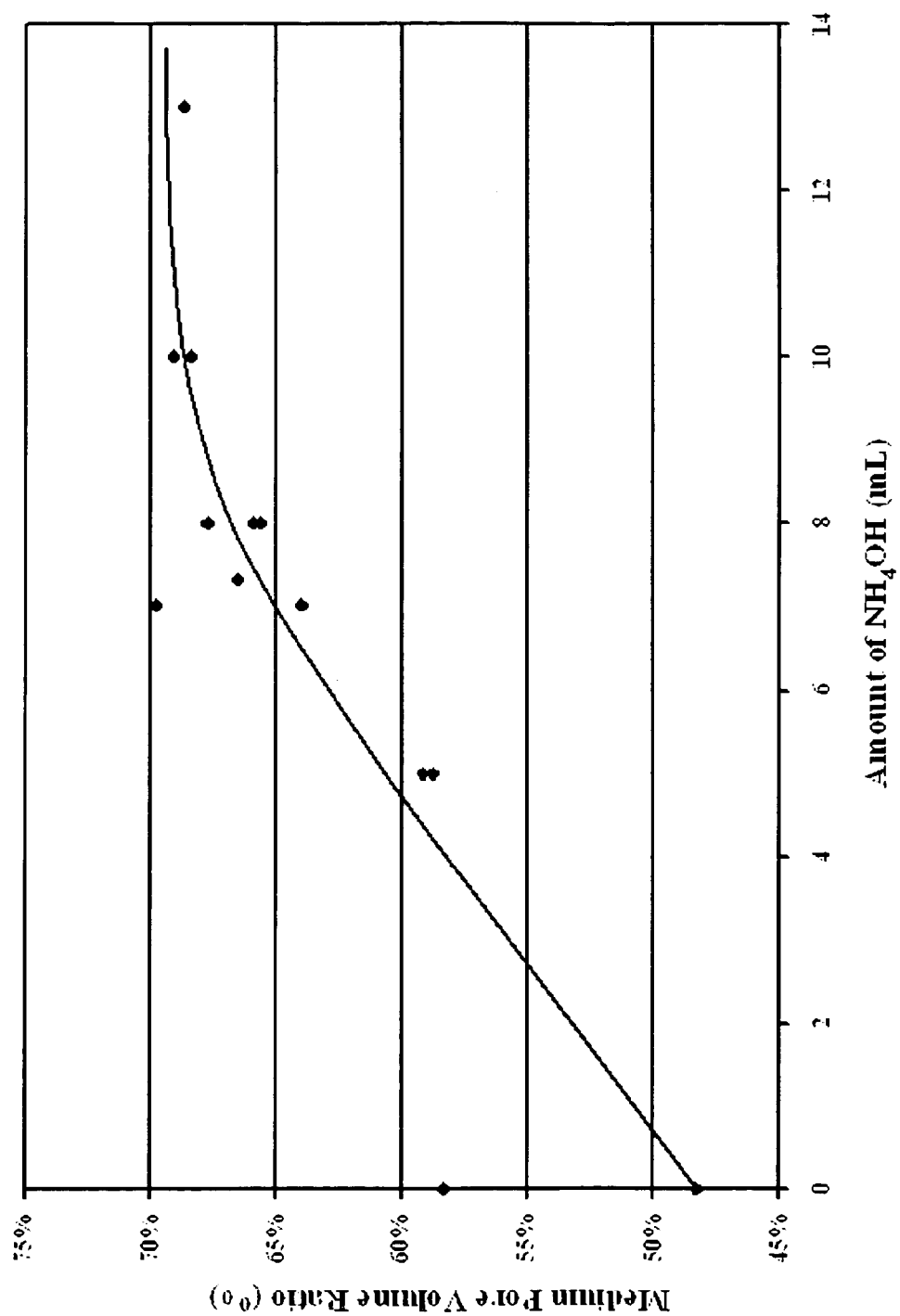
FIG. 2 depicts a graph of % medium pores versus amount of ammonium hydroxide.

Referring now to FIG. 2, a plot of % medium pores relative to all pores versus the amount of ammonium hydroxide added to the catalyst preparation in mL is shown. The plot clearly shows that the addition of ammonium hydroxide, a preferred ammonium-containing compound, is capable of producing catalysts including a pore size distribution having at least 57% medium pores. The data clearly shows that catalysts prepared using between about 4 mL and about 14 mL of ammonium hydroxide having between about 57% and about 70% medium pores.

Figure 3:
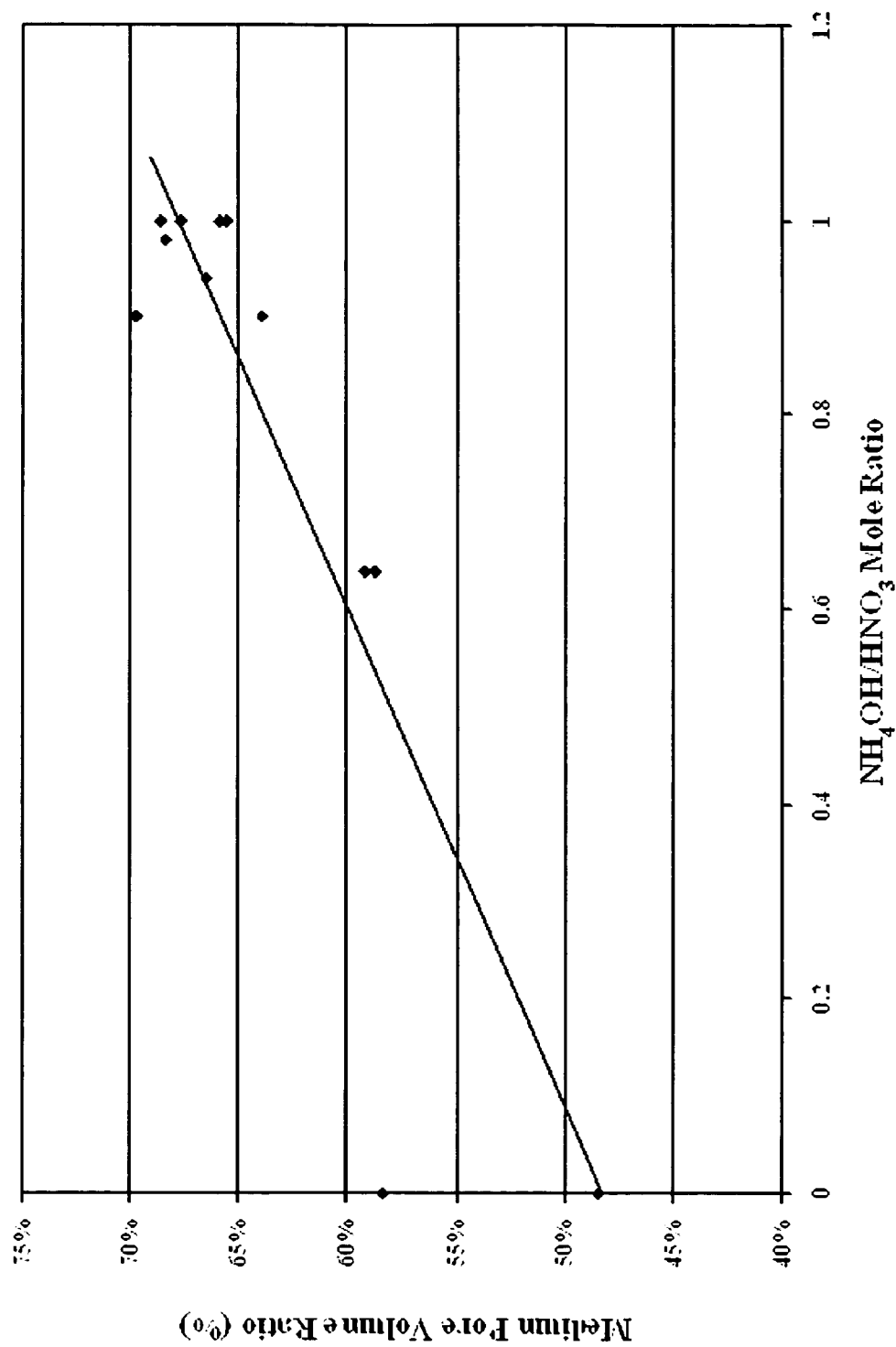
FIG. 3 depicts a graph of % medium pore versus mole ratio of ammonium hydroxide and nitric acid.

Referring now to FIG. 3, a plot of percentage of medium pores versus a mole ratio of ammonium hydroxide and nitric acid. The plot shows that the pore size distribution of the catalyst can be controlled by increasing the mole ratio of ammonium hydroxide and nitric acid from 0 to about 1.0. An especially preferred mole ratio range is between about 0.6 and about 1.0.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A heteropolyacid catalyst comprising at least molybdenum (Mo) and phosphorus (P) adapted to gas-phase oxidize aldehydes to unsaturated acids, where the heteropolyacid catalyst is formed having a pore size distribution comprising at least 55% medium pores.

2. The heteropolyacid catalyst of claim 1, wherein the medium pores have a diameter D greater than or equal to about 100 Å and less than about 1000 Å.

3. The heteropolyacid catalyst of claim 1, further comprising a nitric acid to $Mo_{12}$ mole ratio of at least 6.0:1 in a pre-catalyst material from which the heteropolyacid catalyst was formed.

4. The heteropolyacid catalyst of claim 1, further comprising an effective amount of an ammonium-containing compound added to a pre-catalyst material from which the heteropolyacid catalyst was formed, where the effective amount is sufficient to increase an amount of medium pores in the pore size distribution.

5. The heteropolyacid catalyst of claim 1, wherein the catalyst is prepared using a nitric acid to $Mo_{12}$ mole ratio of at least 6.0:1 and an effective amount of ammonium hydroxide, where the amount is sufficient to adjust the pH to a desired pH value and the effective amount is sufficient to increase an amount of medium pores in the pore size distribution.

6. The heteropolyacid catalyst of claim 1, wherein the catalyst is produced using an amount of nitric acid and an effective amount of ammonium hydroxide and where the amount of nitric acid is sufficient to produce a nitric acid to $Mo_{12}$ mole ratio of at least 6.0:1, where the effective amount of ammonium hydroxide is sufficient to adjust the pH to a desired pH value and where the amount of nitric acid and ammonium hydroxide are sufficient to produce the desired pore size distribution.

7. The heteropolyacid catalyst of claim 1, further comprising vanadium (V).

8. The heteropolyacid catalyst of claim 1, further comprising copper (Cu).

9. The heteropolyacid catalyst of claim 1, further comprising bismuth (Bi).

10. The heteropolyacid catalyst of claim 9, wherein the bismuth is dissolved in a solution having an amount of nitric acid and where the amount of nitric acid is sufficient to produce a nitric acid to $Mo_{12}$ mole ratio of at least 6.0:1 in a pre-catalyst material.

11. The heteropolyacid catalyst of claim 1, further comprising a component selected from the group consisting of potassium (K), rubidium (Rb), cesium (Cs), thallium (Tl), or mixtures or combinations thereof.

12. The heteropolyacid catalyst of claim 1, further comprising a component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof.

13. The heteropolyacid catalyst of claim 1, wherein the aldehydes are selected from the group consisting of acrolein, methacrolein, isobutyraldehyde and mixtures or combinations thereof and where the unsaturated acids are selected from the group consisting of acrylic acid, methacrylic acid, and mixtures or combinations thereof.

14. The heteropolyacid catalyst of claim 1, wherein the catalyst comprises a compound of the general formula:

$$Mo_{12}P_aV_bCu_cBi_dMI_eMII_fO_g \quad (I)$$

where:
MI is selected from the group consisting of potassium (K), rubidium (Rb), cesium (Cs), thallium (Ti), and mixtures or combinations thereof,
MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof, a is a number having a value between about 0.5 and about 3.5,
b is a number having a value between 0.0 and about 5.0,
c is a number having a value between 0.0 and about 1.5,
d is a number having a value between 0.0 and about 2.0,
e is a number having a value between 0.0 and about 2.5,
f is a number having a value between 0.0 and about 5.0,
g is a number having a value representing a sufficient number of oxygen atoms to balance the oxidation state of the catalyst of formula (I), and
where components are acidified by a nitric acid solution including an amount of nitric acid sufficient to produce a nitric acid to $Mo_{12}$ mole ratio of at least 6.0:1 during catalyst preparation and if bismuth is present, then the bismuth component is dissolved in the nitric acid solution prior to adding the nitric acid solution to a solution of some or all of the other components.

15. The heteropolyacid catalyst of claim 14, further comprising an effective amount of an ammonium-containing compound added during catalyst preparation, where the effective amount and the amount of nitric acid are sufficient to produce a pore size distribution comprising at least 57% of medium pores.

16. The heteropolyacid catalyst of claim 15, the medium pores have a diameter D greater than or equal to about 100 Å and less than about 1000 Å.

17. The heteropolyacid catalyst of claim 14, wherein the bismuth component is dissolved in a nitric acid solution, where the amount of nitric acid is sufficient to produce a nitric acid to $Mo_{12}$ mole ratio of at least 6.0:1 during catalyst preparation and an effective amount of an ammonium-containing compound, where the effective amount of the ammonium-containing compound is sufficient to adjust a pH to a desired pH value and where the amount of nitric acid and the amount of ammonium-containing compound are sufficient to produce a pore size distribution comprising at least 55% medium pores.

18. The heteropolyacid catalyst of claim 14, wherein:
a is a number having a value between about 0.5 and about 3.5,
b is a number having a value between about 0.01 and about 5.0,
c is a number having a value between about 0.01 and about 1.5,
d is a number having a value between about 0.01 and about 2.0,
e is a number having a value between about 0.01 and about 2.5, and
f is a number having a value between about 0.01 and about 5.0.

19. The heteropolyacid catalyst of claim 14, wherein:
a is a number having a value between about 0.5 and about 3.5,
b is a number having a value between about 0.1 and about 5.0,
c is a number having a value between about 0.05 and about 1.5,
d is a number having a value between about 0.1 and about 2.0,
e is a number having a value between about 0.1 and about 2.5, and f is a number having a value between about 0.1 and about 5.0.

20. The heteropolyacid catalyst of claim 14, wherein:

a is a number having a value between about 1.0 and about 2.5, b is a number having a value between about 0.1 and about 2.5, c is a number having a value between about 0.05 and about 0.5, d is a number having a value between about 0.1 and about 1.0, e is a number having a value between about 0.2 and about 2.0, and f is a number having a value between about 0.1 and about 2.0.

* * * * *